(12) United States Patent
Rhude et al.

(10) Patent No.: US 8,560,056 B1
(45) Date of Patent: Oct. 15, 2013

(54) INTRACARDIAC DEVICE AND METHOD FOR STORING CARDIAC TEST RESULTS AND ASSOCIATED EGM DATA

(75) Inventors: Jennifer Rhude, Castaic, CA (US); Elia A. Mouchawar, Valencia, CA (US); David Houck, Millburn, NJ (US); Gregory Hauck, Valencia, CA (US); Tejpal Singh, Stevenson Ranch, CA (US); Monique Prue, Sherman Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/564,446

(22) Filed: Aug. 1, 2012

Related U.S. Application Data

(62) Division of application No. 11/467,739, filed on Aug. 28, 2006, now Pat. No. 8,260,407.

(60) Provisional application No. 60/716,448, filed on Sep. 12, 2005.

(51) Int. Cl.
*A61B 5/04* (2006.01)
*A61N 1/00* (2006.01)

(52) U.S. Cl.
USPC .............................. 600/510; 600/509; 607/11

(58) Field of Classification Search
USPC ..................................... 607/11; 600/509–510
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,825,869 A | 5/1989 | Sasmor et al. | |
| 4,940,052 A | 7/1990 | Mann et al. | |
| 4,944,298 A | 7/1990 | Sholder | |
| 5,012,814 A | 5/1991 | Mills et al. | |
| 5,224,486 A | 7/1993 | Lerman et al. | |
| 5,320,643 A | 6/1994 | Roline et al. | |
| 5,431,691 A | 7/1995 | Snell et al. | |

(Continued)

FOREIGN PATENT DOCUMENTS

| | | |
|---|---|---|
| DE | 3236322 A1 | 4/1984 |
| DE | 3636996 C1 | 11/1987 |

(Continued)

OTHER PUBLICATIONS

Fraser, Jennifer D. RN et al., "Guidelines for pacemaker follow-up in Canada: A consensus statement of the Canadian Working Group on Cardiac Pacing," Can. J. Cardio. 2000;16(3):355-363.

(Continued)

*Primary Examiner* — Nicole F Lavert

(57) ABSTRACT

In a possible implementation, a method for cardiac testing is provided which includes measuring test data associated with cardiac events and storing the test data in an intracardiac stimulation device. The method further includes acquiring event electrograms corresponding with the test data and storing the event electrograms corresponding with the test data in the intracardiac stimulation device. In a possible implementation, marker data is stored associating event electrograms with measured test data, which may identify the event electrograms used for measuring the test data and/or identify when adjacent event electrograms are not contiguous. In some implementations, the test data may be measured and stored in an out-of-clinic test, and the test data and the corresponding event electrograms may be later retrieved from the intracardiac stimulation device and presented on a visual display.

4 Claims, 9 Drawing Sheets

(56) References Cited

U.S. PATENT DOCUMENTS

| | | | |
|---|---|---|---|
| 5,456,261 | A | 10/1995 | Luczyk |
| 5,466,254 | A | 11/1995 | Helland |
| 5,476,483 | A | 12/1995 | Bornzin et al. |
| 5,487,754 | A | 1/1996 | Snell et al. |
| 5,564,430 | A | 10/1996 | Jacobson et al. |
| 5,674,254 | A | 10/1997 | van Krieken |
| 5,683,431 | A | 11/1997 | Wang |
| 5,697,959 | A | 12/1997 | Poore |
| 5,702,427 | A | 12/1997 | Ecker et al. |
| 5,713,933 | A * | 2/1998 | Condie et al. ............ 607/28 |
| 5,732,708 | A | 3/1998 | Nau et al. |
| 5,785,660 | A | 7/1998 | van Lake et al. |
| 5,833,623 | A | 11/1998 | Mann et al. |
| 5,891,178 | A | 4/1999 | Mann et al. |
| 5,944,744 | A | 8/1999 | Paul et al. |
| 5,944,745 | A | 8/1999 | Rueter |
| 5,974,341 | A | 10/1999 | Er et al. |
| 6,101,415 | A | 8/2000 | Er et al. |
| 6,243,606 | B1 | 6/2001 | Mann et al. |
| 6,259,950 | B1 | 7/2001 | Mann et al. |
| 6,263,244 | B1 | 7/2001 | Mann et al. |
| 6,285,908 | B1 | 9/2001 | Mann et al. |
| 6,308,100 | B1 | 10/2001 | Er et al. |
| 6,314,323 | B1 | 11/2001 | Ekwall |
| 6,526,314 | B1 | 2/2003 | Eberle et al. |
| 6,529,771 | B1 | 3/2003 | Kieval et al. |

FOREIGN PATENT DOCUMENTS

| | | |
|---|---|---|
| EP | 0565084 A2 | 10/1993 |
| EP | 0565084 A3 | 10/1994 |
| EP | 0832600 B1 | 4/2004 |
| WO | 2005022438 A1 | 3/2005 |

OTHER PUBLICATIONS

Gregoratos, Gabriel MD FACC et al., "ACC/AHA Guidelines for Implantation of Cardiac Pacemakers and Antiarrhythmia Devices—A Report of the American College of Cardiology/American Heart Association Task Force on Practice Guidelines (Committee on Pacemaker Implantation)," JACC. 1998;31(5):1175-1209.

NonFinal Office Action, mailed Sep. 26, 2008—Parent U.S. Appl. No. 11/467,739.

Restriction Requirement, mailed Jul. 8, 2009—Parent U.S. Appl. No. 11/467,739.

NonFinal Office Action, mailed Nov. 25, 2009—Parent U.S. Appl. No. 11/467,739.

Final Office Action, mailed Oct. 4, 2010—Parent U.S. Appl. No. 11/467,739.

Notice of Allowance, mailed Jul. 19, 2012—Parent U.S. Appl. No. 11/467,739.

\* cited by examiner

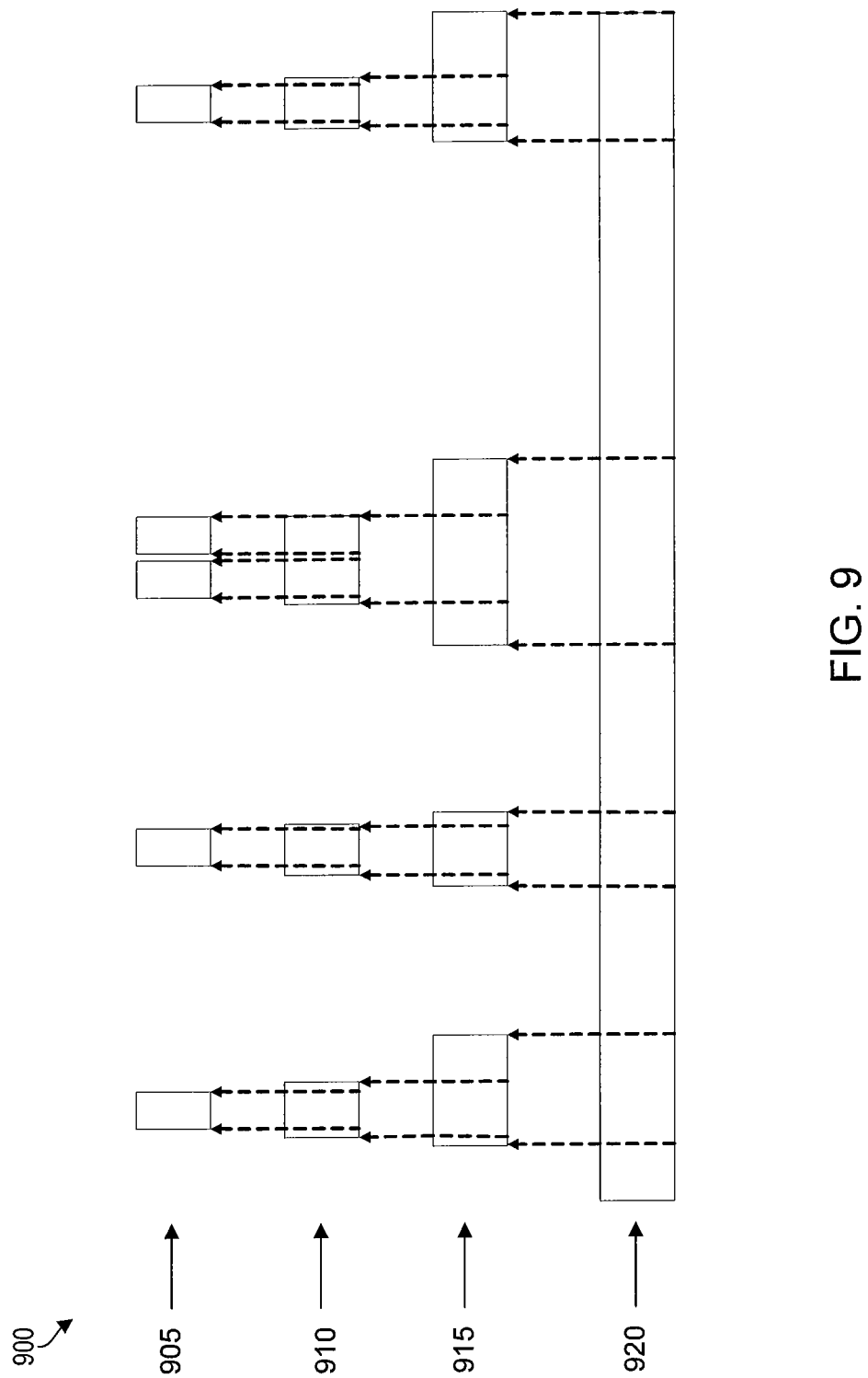

INTRACARDIAC DEVICE AND METHOD FOR STORING CARDIAC TEST RESULTS AND ASSOCIATED EGM DATA

CROSS-REFERENCES TO RELATED APPLICATIONS

This application is a division of U.S. patent application Ser. No. 11/467,739, filed Aug. 28, 2006, now U.S. Pat. No. 8,260,407, which claims priority to U.S. Provisional Application Ser. No. 60/716,448, filed Sep. 12, 2005, and is related to U.S. patent application Ser. No. 13/564,417, filed Aug. 1, 2012, titled "Intracardiac Device and method for Storing Cardiac Test Results and Associated EGM Data."

BACKGROUND

Over the past several decades thousands of patients have been fitted with implantable cardiac pacing, cardioversion, defibrillation and/or other devices that can deliver cardiac therapy. Monitoring of such patients often involves a collaborative effort of physicians, nurses, device manufacturers, regulatory agencies, insurance companies and health care institution managers. Patients may receive care through in-person office visits, telephone consultations or other communication routes (e.g., the Internet, etc.). Care is often scheduled on a periodic basis, although office visits may occur less frequently than distance consultations (e.g., typically at least four times per year). During an office or a distance consultation, automated analyses may be performed in which an implanted device communicates with a receiver and/or transmitter unit, which is typically connected to a computer. Aside from such procedures, little else involving patient care is automated. For example, care providers typically need to follow extensive written guidelines on how to assess a patient's condition and/or the condition of an implanted device (e.g., follow-up guidelines). Further, information collected by a care provider typically requires performance of certain assessments and associated data entry during and/or after a consultation. Such assessments require a substantial time commitment and patient care provider interaction. Further, the associated data entry can require a significant amount of care provider time.

One such assessment involves the patient care provider verifying device programming and functionality by performing a series of tests utilizing the device and the programmer after the device has been implanted in the patient. These tests include measuring amplitudes of intrinsic cardiac events, such as P-waves, naturally occurring in the patient's heart as well as capture thresholds of pacing pulses required to generate a cardiac response. These tests are time consuming.

Such tests take time in the clinic because the physician has to observe the test being performed, and then analyze and print the results, which include intracardiac electrograms. The physician receives a result, such as, for example, a P-wave amplitude in the form of a numeric value, and also is able to see the events used to obtain that result via real-time markers and electrograms.

To verify the validity of the test data measured by the device, the physician retrieves the test data from the device, generates intracardiac electrograms of the patient's heart, and compares the test data with the intracardiac electrograms. For example, the physician may examine the intracardiac electrogram to verify the morphology of a cardiac event and to determine whether the test data corresponds to the cardiac event.

One possible way to reduce the time spent by the physician is to make these same measurements outside the clinic. The pacemaker can perform measurements outside the clinic and store the numerical results in the pacemaker for later viewing by the physician. Currently, with an outside the clinic measurement, when the physician interrogates the device, a numerical result is provided. For example, the result may indicate that the ventricular capture threshold is 0.875 V. Since the measurement was made while the patient was away from the clinic, the electrogram and marker data for the events used to obtain these measurements is not available. As such, the physician is not able to assess whether the events measured were truly P-waves, or to have printouts of the measured events available for inclusion in the patient's record.

In light of the above, a need exists for collection and/or analysis of automatically generated test data from an intracardiac stimulation device that allows a patient care provider to verify the test data in a time efficient manner.

SUMMARY

In a possible implementation, a method for cardiac testing is provided which includes measuring test data associated with cardiac events and storing the test data in an intracardiac stimulation device. The method further includes acquiring event electrograms corresponding with the test data and storing the event electrograms corresponding with the test data in the intracardiac stimulation device. This method may include storing marker data associating event electrograms with measured test data. The marker data may identify the event electrograms used for measuring the test data and/or identify when adjacent event electrograms are not contiguous. The test data may be measured and stored in an out-of-clinic test, and the test data and the corresponding event electrograms may be later retrieved from the intracardiac stimulation device. The test data and at least a portion of the corresponding event electrograms may be presented on a visual display.

In some implementations, a method for cardiac testing is provided which includes performing a cardiac test and recording the measured test result from the test in the cardiac device along with recording non-contiguous electrogram data corresponding with the cardiac event complexes used to obtain the measured test result. Marker data associated with the non-contiguous electrogram data is also recorded. This may include storing marker data which identifies when adjacent event electrograms are not contiguous. In some implementations, the method may further include retrieving the non-contiguous electrogram data and displaying at least a portion of the non-contiguous electrogram data. The displayed non-contiguous electrogram data may be used to confirm the measured test result. The cardiac test may be an out-of-clinic test, such as a capture threshold or a measurement of an intrinsic event.

In a possible embodiment, a cardiac stimulation device includes a pulse generator configured to generate a pacing pulse and a processor configured such that the cardiac stimulation device is capable of measuring test data associated with cardiac events, acquiring non-contiguous event electrograms corresponding with the test data, and storing the test data and the non-contiguous event electrograms into memory in the cardiac stimulation device. The marker data may associate event electrograms with measured test data and indicate when adjacent event electrograms are not contiguous.

In a possible embodiment, a cardiac stimulation device is provided which includes a means for measuring test data associated with cardiac events. This embodiment further includes a means for acquiring event electrograms corresponding to the cardiac events and a means for storing in the cardiac stimulation device, the test data and non-contiguous relevant event electrograms corresponding to the cardiac event. In some embodiments, the means for storing the event electrogram further includes a means for storing a marker associated with the event electrogram, which may indicate when adjacent event electrograms are not contiguous.

BRIEF DESCRIPTION OF THE DRAWINGS

Features and advantages of the described implementations can be more readily understood by reference to the following description taken in conjunction with the accompanying drawings.

FIG. 9 is a diagram of data storage and retrieval of intracardiac electrogram data.

DETAILED DESCRIPTION

For an effective out-of-clinic test, it is necessary to allow a physician to verify the measured numerical values with the corresponding electrogram data. Display of electrogram data for out of clinic test is discussed in U.S. patent application Ser. No. 10/762,101, filed Jan. 20, 2004, entitled "Implantable Device Diagnostics for Instant Follow-Up," now abandoned, herein incorporated by reference.

As some tests can take a long time, storing electrogram data continuously from the beginning of a test to the end of a test requires a sizable amount of storage capacity within an implanted cardiac device. Furthermore, if data are continuously collected from the beginning of an out-of-clinic test until the end of the test, it would necessitate a considerable amount of display capacity, require a long time to retrieve all the data, and require time by the physician to sort through a large amount of electrogram data to view the relevant electrogram event data.

In some tests that may be performed out-of-clinic, although the test itself may take a long time to complete, the event electrogram data used for measurements can be spaced apart, with one or more intervening events electrograms between the measured electrogram data that are not used to obtain a test measurement. As such, a physician may be required to spend time sorting through electrogram data for intervening events that were not used to obtain test measurements. Further, cardiac device memory contains electrogram data for events that occurred during a test period but that are not associated with an actual test measurement. Thus, it is possible to store and provide test results in a more concise and efficient manner to reduce in-clinic workload, in accordance with the discussion below.

Overview of Intracardiac Stimulation Device

Figure 1:
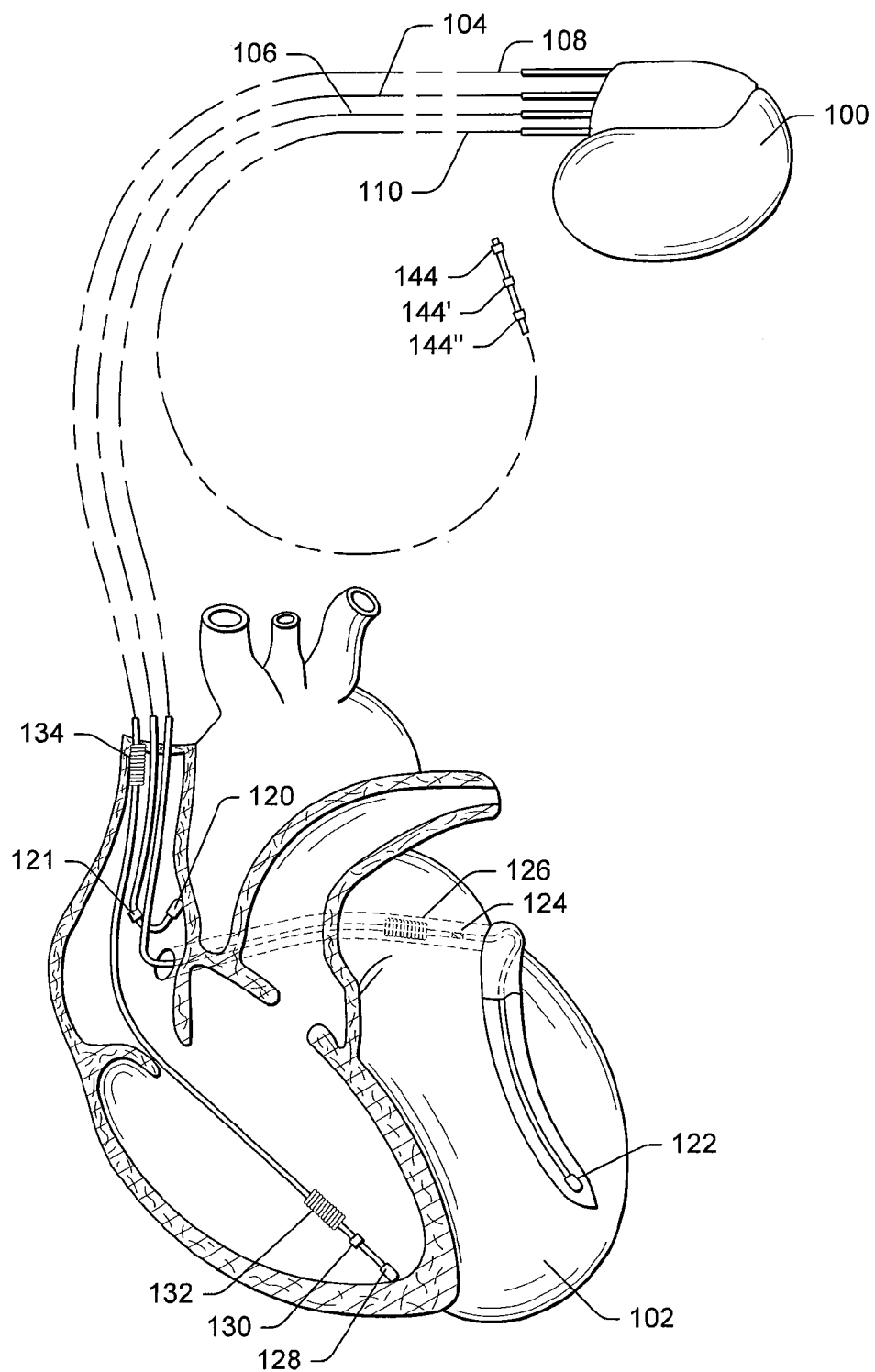
FIG. 1 is a simplified diagram illustrating an exemplary intracardiac stimulation device in electrical communication with a patient's heart.

FIG. 1 shows an exemplary intracardiac stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses, such as pacing pulses, suitable for stimulation of autonomic nerves. In addition, the intracardiac stimulation device 100 includes a fourth lead 110 having, in this implementation, three electrodes 144, 144', 144" suitable for stimulation of autonomic nerves and/or detection of other physiologic signals that may be used to modify pacing parameters of the intracardiac stimulation device 100. The fourth lead 110 may be positioned in and/or near a patient's heart 102 or near an autonomic nerve within a patient's body and remote from the heart 102. The right atrial lead 104, as the name implies, is positioned in and/or passes through a patient's right atrium. The right atrial lead 104 optionally senses atrial cardiac signals and/or provides right atrial chamber stimulation therapy. As shown in FIG. 1, the intracardiac stimulation device 100 is coupled to an implantable right atrial lead 104 having, for example, an atrial tip electrode 120, which typically is implanted in the patient's right atrial appendage. The right atrial lead 104, as shown in FIG. 1, also includes an atrial ring electrode 121. The right atrial lead 104 may have other electrodes as well. For example, the right atrial lead 104 may optionally include a distal bifurcation having electrodes suitable for stimulation of autonomic nerves.

To sense atrial cardiac signals, ventricular cardiac signals and/or to provide chamber pacing therapy, particularly on the left side of a patient's heart 102, the intracardiac stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. An exemplary coronary sinus lead 106 is described in U.S. Pat. No. 5,466,254, "Coronary Sinus Lead with Atrial Sensing Capability" (Helland), which is incorporated by reference herein. The coronary sinus lead 106 may optionally include electrodes for stimulation of autonomic nerves, may include pacing and autonomic nerve stimulation functionality, and may further include bifurcations or legs. For example, an exemplary coronary sinus lead 106 may include pacing electrodes capable of delivering pacing pulses to a patient's left ventricle and at least one electrode capable of stimulating an autonomic nerve. An exemplary coronary sinus lead 106 (or left ventricular lead or left atrial lead) may also include at least one electrode capable of stimulating an autonomic nerve of the heart 102. Such an electrode may be positioned on the coronary sinus lead 106 or on a bifurcation or leg of the coronary sinus lead 106. FIG. 1 is shown for example purposes. Other implementations (not shown) are possible. For example, a left ventricular ring electrode (not shown) may be included, and the left atrial ring 124 and coil electrode 126 (and left atrial tip, not shown) could be excluded.

The cardiac stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead 108 may also include at least one electrode capable of stimulating an autonomic nerve of the heart 102. Such an electrode may be positioned on the right ventricle lead 108 or on a bifurcation or leg of the right ventricle lead 108.

Figure 2:
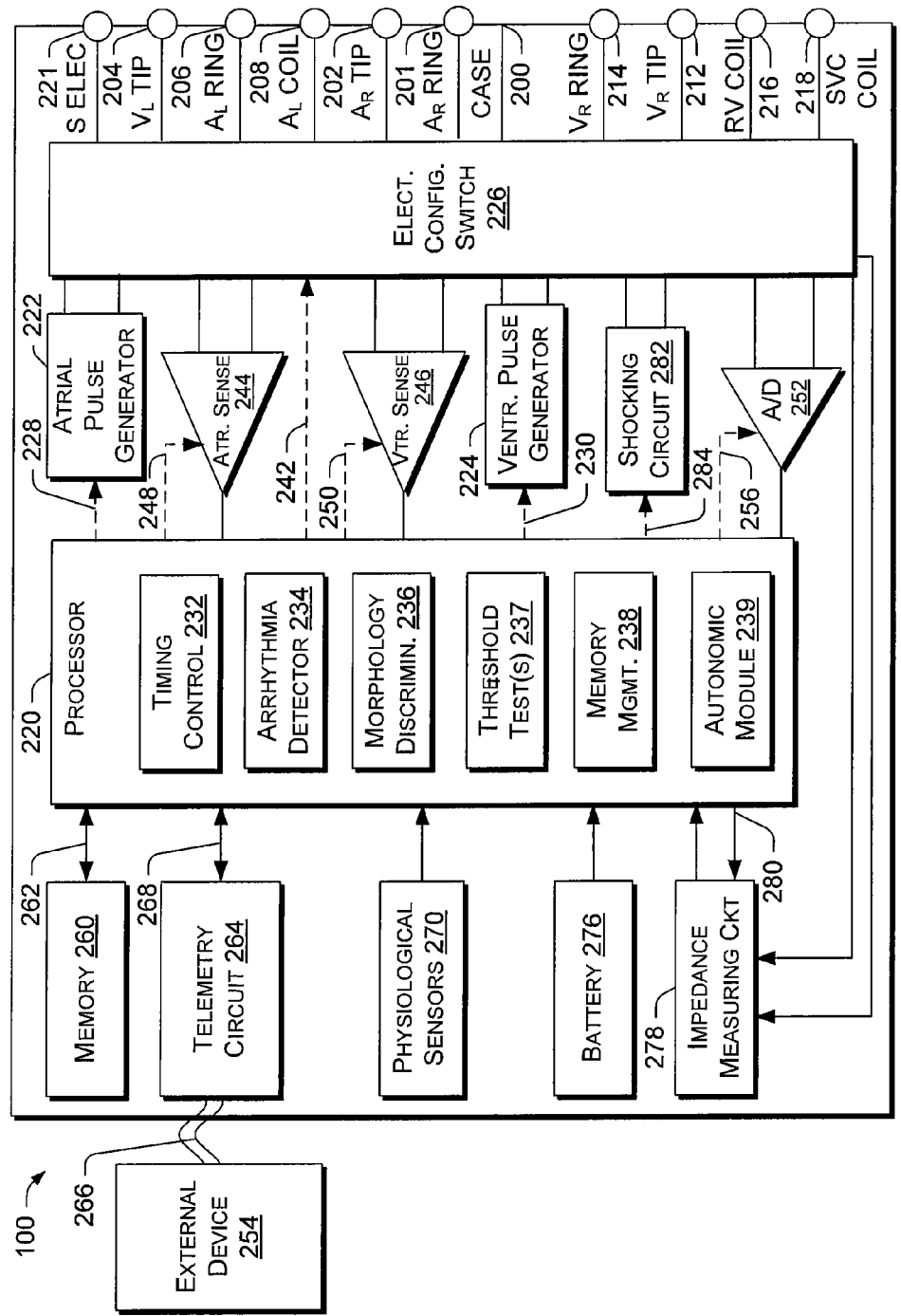
FIG. 2 is a functional block diagram of the exemplary intracardiac stimulation device.

FIG. 2 shows an exemplary, simplified block diagram depicting various components of the intracardiac stimulation device 100. The intracardiac stimulation device 100 can be capable of treating both fast and slow arrhythmias with stimulation therapy, including cardioversion, defibrillation, and pacing stimulation. The intracardiac stimulation device 100 can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable intracardiac stimulation device 100. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

The intracardiac stimulation device 100 includes a housing 200, often referred to as a "can", "case" or "case electrode", and may be programmably selected to act as the return electrode for all "unipolar" modes. The housing 200 may further be used as a return electrode alone or in combination with one or more of the coil electrodes 126, 132 and 134 for shocking purposes. The housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 configured for connection to the atrial tip electrode 120. A right atrial ring terminal (AR RING) 201 is also shown, which is configured for connection to the atrial ring electrode 121. To achieve left chamber sensing, pacing, shocking, and/or autonomic stimulation, the connector includes at least a left ventricular tip terminal (VL TIP) 204, a left atrial ring terminal (AL RING) 206, and a left atrial shocking terminal (AL COIL) 208, which are configured for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal (S ELEC) 221.

To support right chamber sensing, pacing, shocking, and/or autonomic nerve stimulation, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are configured for connection to the right ventricular tip electrode 128, the right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal 221).

At the core of the intracardiac stimulation device 100 is a processor 220 that controls the various modes of stimulation therapy. The processor 220 may be a programmable microcontroller including a microprocessor, or equivalent control circuitry, designed specifically for controlling the delivery of stimulation therapy, and may further include RAM or ROM memory, logic and timing circuitry, state machine circuitry, and I/O circuitry. Typically, the processor 220 includes the ability to process or monitor input signals (data or information) as controlled by a program code stored in a designated block of memory. The type of processor is not critical to the described implementations. Rather, any suitable processor 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.), and the control system of U.S. Pat. No. 4,944,298 (Sholder), all of which are incorporated by reference herein. A description of the various timing intervals which may be used within the intracardiac stimulation device 100 is described in U.S. Pat. No. 4,788,980 (Mann et al.), which is incorporated by reference herein.

The intracardiac stimulation device 100 includes an atrial pulse generator 222 and a ventricular pulse generator 224 that generate electrical pacing pulses for delivery to a patient's heart 102 by the right atrial lead 104, the coronary sinus lead 106, and/or the right ventricular lead 108 via an electronic configuration switch (Elect. Config. Switch) 226. To provide stimulation therapy in each of the four chambers of the heart 102 (or to autonomic nerves), the atrial and ventricular pulse generators 222 and 224 may include dedicated, independent pulse generators, multiplexed pulse generators, or shared pulse generators. The pulse generators 222 and 224 are controlled by the processor 220 via appropriate control signals 228 and 230, respectively, to trigger or inhibit the pacing pulses.

The processor 220 further includes timing control circuitry 232 to control the timing of the pacing pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

The processor 220 further includes an arrhythmia detector 234 and may optionally include an orthostatic compensator (not shown) and a minute ventilation (MV) response module (not shown). These components can be utilized by the intracardiac stimulation device 100 for determining desirable times to administer various therapies, including those to reduce the effects of orthostatic hypotension. The aforementioned components may be implemented in hardware as part of the processor 220, or as software/firmware instructions programmed into the intracardiac stimulation device 100 and executed on the processor 220 during certain modes of operation.

Processor 220 further includes a morphology discrimination module 236, a threshold test module 237, and a memory management module 238. These modules are optionally used to implement various exemplary recognition algorithms and/or methods presented below. For example, the threshold test module 237 may perform a capture threshold test or sensing threshold test. The morphology discrimination module 236, the threshold test module 237, and the memory management module 238 may be implemented in hardware as part of the processor 220, or as software/firmware instructions programmed into the intracardiac stimulation device 100 and executed on the processor 220 during certain modes of operation.

Processor 220 further includes an autonomic nerve stimulation module 239 for performing a variety of tasks related to autonomic nerve stimulation. This component can be utilized by the intracardiac stimulation device 100 for determining desirable times to administer various therapies, including, but not limited to, parasympathetic stimulation. The autonomic nerve stimulation module 239 may be implemented in hardware as part of the processor 220, or as software/firmware instructions programmed into the intracardiac stimulation device 100 and executed on the processor 220 during certain modes of operation.

The electronic configuration switch 226 includes a plurality of switches for connecting the desired electrodes to the appropriate I/O circuits, thereby providing complete electrode programmability. Accordingly, the switch 226, in response to a control signal 242 from the processor 220, determines the configuration of the stimulation pulses (e.g., unipolar, bipolar, etc.) by selectively closing the appropriate combination of switches (not shown) as is known in the art.

The intracardiac stimulation device 100 may also include an atrial sensing circuit (ATR. SENSE) 244 and a ventricular sensing circuit (VTR. SENSE) 246 selectively coupled to the right atrial lead 104, the coronary sinus lead 106, and the right ventricular lead 108, through the switch 226 for detecting the presence of cardiac events in each of the four chambers of the heart 102. Accordingly, the atrial sensing circuit 244 and the ventricular sensing circuit 246 may include dedicated sense amplifiers, multiplexed amplifiers, or shared amplifiers. The switch 226 determines the "sensing configuration" of the cardiac signal by selectively closing the appropriate switches, as is also known in the art. In this way, the clinician may program the sensing configuration independent of the stimulation configuration.

Each of the atrial sensing circuit 244 and ventricular sensing circuit 246 preferably employs one or more low power, precision amplifiers with programmable gain and/or automatic sense control, bandpass filtering, and a threshold detection circuit, as known in the art, to selectively sense the cardiac signal of interest. The automatic sense control enables the intracardiac stimulation device 100 to deal effectively with the difficult problem of sensing the low amplitude signal characteristics of atrial or ventricular fibrillation.

The outputs of the atrial sensing circuit 244 and ventricular sensing circuit 246 are connected to the processor 220, which, in turn, is able to trigger or inhibit the atrial pulse generator 222 and the ventricular pulse generator 224, respectively, in a demand fashion in response to the absence or presence of cardiac events in the appropriate chambers of the heart 102. Furthermore, as described herein, the processor 220 is also capable of analyzing information output from the atrial sensing circuit 244, the ventricular sensing circuit 246, and/or a data acquisition system (A/D) 252 to determine or detect whether and to what degree tissue capture has occurred and to program a pulse, or pulses, in response to such determinations. The atrial sensing circuit 244 and the ventricular sensing circuit 246, in turn, receive control signals 248 and 250 from the processor 220 for controlling the gain, threshold, polarization charge removal circuitry (not shown), and timing of any blocking circuitry (not shown) coupled to the inputs of the atrial sensing circuit 244 and the ventricular sensing circuit 246, as is known in the art.

For arrhythmia detection, the intracardiac stimulation device 100 may utilize the atrial sensing circuit 244 and the ventricular sensing circuit 246 to sense cardiac signals and to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

Such an exemplary detection module 234, optionally uses timing intervals between sensed events (e.g., P-waves, R-waves, and depolarization signals associated with fibrillation which are sometimes referred to as "F-waves" or "Fib-waves") and to perform one or more comparisons to a predefined rate zone limit (i.e., bradycardia, normal, low rate VT, high rate VT, and fibrillation rate zones) and/or various other characteristics (e.g., sudden onset, stability, physiological sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention. Such a module is optionally suitable for performing various exemplary methods described herein. For example, such a module optionally allows for analyses related to action potentials (e.g., MAPs, T waves, etc.) and characteristics thereof (e.g., alternans, activation times, repolarization times, derivatives, etc.).

Cardiac signals are also applied to inputs of the data acquisition system 252. The data acquisition system 252 is configured to acquire intracardiac electrogram signals, convert the raw analog data into a digital signal, and store the digital signals for later processing, transmission to the processor 220, and/or telemetric transmission to an external device 254. The digital signals stored in the data acquisition system 252 may be an intracardiac event electrogram (IEGM). The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The processor 220 is further coupled to a memory 260 by a suitable computer bus 262 (e.g., an data/address bus), wherein the programmable operating parameters used by the processor 220 are stored and modified, as required, in order to customize the operation of the intracardiac stimulation device 100 to suit the needs of a particular patient. Such operating parameters define, for example, pacing pulse amplitude, pulse duration, electrode configuration, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the intracardiac stimulation device 100 may be non-invasively programmed into the memory 260 through a telemetry circuit 264 in telemetric communication via communication link 266 with the external device 254, such as a programmer, transtelephonic transceiver, or a diagnostic system analyzer. The processor 220 activates the telemetry circuit 264 with a control signal 268. The telemetry circuit 264 advantageously allows IEGMs, test data, and status information relating to the operation of the intracardiac stimulation device 100 (as contained in the processor 220 or memory 260) to be sent to the external device 254 through an established communication link 266.

The intracardiac stimulation device 100 can further include a physiological sensor 270, commonly referred to as a "rate-responsive" sensor because it is typically used to adjust pacing stimulation rate according to the exercise state of the patient. The physiological sensor 270 may further be used to detect changes in cardiac output. For example, U.S. Pat. No. 6,314,323 to Ekwall, entitled "Heart stimulator determining cardiac output, by measuring the systolic pressure, for controlling the stimulation", which issued Nov. 6, 2001, discusses a pressure sensor adapted to sense pressure in a right ventricle and to generate an electrical pressure signal corresponding to the sensed pressure. An integrator supplied with the pressure signal integrates the pressure signal between a start time and a stop time to produce an integration result that corresponds to cardiac output, changes in the physiological condition of the heart, or diurnal changes in activity (e.g., detecting sleep and wake states). Accordingly, the processor 220 responds by adjusting the various pacing parameters (such as rate, AV Delay, V-V Delay, etc.) at which the atrial and ventricular pulse generators 222 and 224 generate stimulation pulses.

While shown as being included within the intracardiac stimulation device 100, it is to be understood that the physiological sensor 270 may also be external to the intracardiac stimulation device 100, yet still be implanted within or carried by the patient. Examples of physiological sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. An exemplary activity variance sensor is described in U.S. Pat. No. 5,476,483 (Bornzin et al.), issued Dec. 19, 1995, which is incorporated by reference herein.

More specifically, the physiological sensor 270 may optionally include sensors for detecting movement and minute ventilation in the patient. The physiological sensor 270 may include a position sensor and/or a minute ventilation (MV) sensor to sense minute ventilation, which is defined as the total volume of air that moves in and out of a patient's lungs in a minute. Signals generated by the position sensor and MV sensor are passed to the processor 220 for analysis in determining whether to adjust the pacing rate, etc. The processor 220 monitors the signals for indications of the patient's position and activity status, such as whether the patient is climbing upstairs or descending downstairs or whether the patient is sitting up after lying down.

The intracardiac stimulation device 100 additionally includes a battery 276 that provides operating power to the circuits shown in FIG. 2. For the intracardiac stimulation device 100, which employs shocking therapy, the battery 276 is capable of operating at low current drains for long periods of time (e.g., preferably less than 10 mA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The intracardiac stimulation device 100 can further include magnet detection circuitry (not shown), coupled to the processor 220, to detect when a magnet is placed over the intracardiac stimulation device 100. A magnet may be used by a clinician to perform various test functions of the intracardiac stimulation device 100.

The intracardiac stimulation device 100 further includes an impedance measuring circuit 278 that is enabled by the processor 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the intracardiac stimulation device 100 is intended to operate as an implantable cardioverter/defibrillator (ICD) device, it detects the occurrence of an arrhythmia, and automatically applies an appropriate therapy to the heart 102 aimed at terminating the detected arrhythmia. To this end, the processor 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the processor 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level, and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the processor 220 is capable of controlling the synchronous or asynchronous delivery of the shocking pulses.

The intracardiac stimulation device 100 is surgically implanted in a patient and is programmed to sense cardiac events in the patient's heart 102 and to generate pacing pulses to control the rhythm of the patient's heart 102. In the programming process, operating parameters are provided to the intracardiac stimulation device 100 for sensing the cardiac events and generating the pacing pulses. These programming parameters include expected amplitudes of cardiac events, such as P-waves, along with capture thresholds for evoking the cardiac events. For example, the intracardiac stimulation device 100 may periodically deliver a pacing pulse to the patient's heart 102, measure test data and an IEGM for a cardiac event occurring in response to the pacing pulse, and store the test data along with the IEGM in the memory 260.

Storage and Retrieval of Test Data and Intracardiac Event Electrograms

As discussed briefly above, a physician typically performs some measurements on the patient in a follow-up visit with the patient. These measurements include amplitudes of intrinsic waveforms, as well as determination of the pacing amplitude necessary to elicit a cardiac response (capture threshold). The tests can take a few minutes to perform, and the physician typically spends several minutes analyzing the test results.

Alternatively, the measurements may be taken in an out-of-clinic environment. In the out-of-clinic environment, the tests still take a great deal of time to perform, but the physician is not present. Saving all IEGM and marker data from a relatively long out-of-clinic test (e.g., AutoCapture™ tests, AutoPR, etc.) is not desirable as it will save a large amount of unwanted and unnecessary information. For example, an automatic capture threshold test can take up to two minutes or more, and storing all of this data would be a waste of device memory. In addition, during a subsequent office visit, it would take a long time to retrieve the data, and most of the data will be irrelevant.

In various embodiments, the intracardiac stimulation device 100 selectively measures and stores test data, which may be used to adjust the operating parameters such that the intracardiac stimulation device 100 operates properly in the patient. The test data may include amplitudes of the intrinsic cardiac events and capture thresholds for each pacing chamber. (Thus, in various embodiments, the intracardiac stimulation device 100 is capable of automatically assessing the amplitude of intrinsic cardiac events and of automatically assessing the pacing capture threshold.) The intracardiac stimulation device 100 also stores IEGMs of the cardiac events, which may include markers indicating characteristics of the cardiac events. A physician can then use the stored IEGMs to verify the test data in a follow-up office visit with the patient instead of performing the test and generating the IEGMs during the follow-up office visit. Furthermore, selective storage of the test data and the IEGMs in the intracardiac stimulation device 100 minimizes the time for retrieving the test data and IEGMs during the follow-up office visit.

The intracardiac stimulation device 100 may selectively store test data and IEGMs for cardiac events. This process may occur automatically on a periodic basis, such as once day or once every few hours. Selectively storing the test data and the IEGMs reduces a size requirement of the memory 260 and a time period for retrieving the test data and the IEGMs from the intracardiac stimulation device 100.

Additionally, storing test data for selected relevant events into the memory 160 may also minimize overhead in the processor 220 and may increase the battery life of the intracardiac stimulation device 100. Moreover, a patient care provider may not need to perform the test to generate IEGMs during a follow-up patient counseling session to verify the test results from the automatic test. This is because the patient care provider or physician can use the IEGM retrieved from the intracardiac stimulation device 100.

Figure 3:
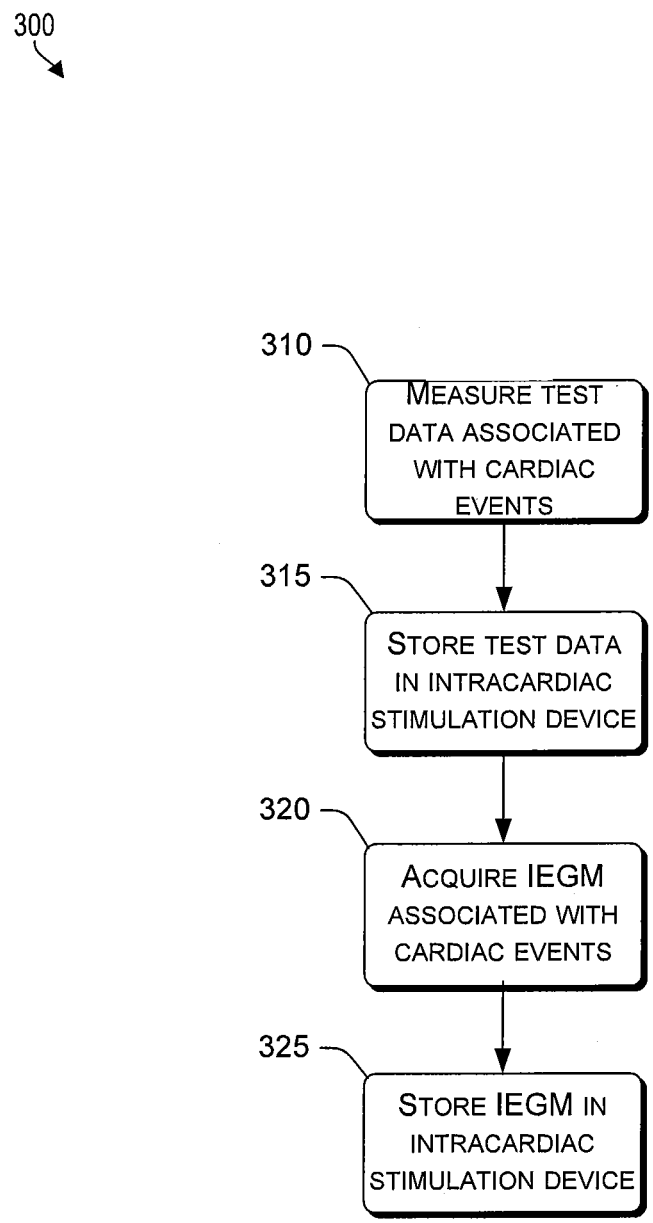
FIG. 3 is a flow chart for an exemplary method of performing a capture threshold test.

Turning to FIG. 3, in one example implementation 300, a cardiac test, such as a capture threshold test, is run. In some implementations, the cardiac test may be performed out of clinic, which may be initiated by the expiration of the timer, in accordance with a schedule, or by a triggering event, or signal. To perform the capture threshold test, a series of pacing pulses, i.e. test pulses, at varying amplitudes will need to be output by the device 100. The device 100 identifies when a test pacing pulse should be delivered, and delivers the test pacing pulses. Thus, the device 100 generates a series of test pulses having varying amplitudes and spaced with regard to a number of cardiac cycles (e.g., once every 16 cardiac cycles), or with regard to a timer, etc.

The device 100 measures test data associated with the cardiac event 310, such as whether capture occurred, and stores the measured test data, at step 315. In the case of the capture threshold test, this may include storing the pacing amplitude along with the indication of whether capture occurred.

In step 320, an IEGM associated with the cardiac event is acquired for a time window around the pacing pulse. The IEGM may be acquired for one or more cardiac cycles before and after the pacing pulse, if desired. The test data may be measured and stored at the same time, and concurrent with steps 320 and 325. In step 325, the IEGM associated with the cardiac event is stored in the intracardiac stimulation device 100. For example, the IEGM data may be stored starting about one second before a pacing pulse and ending one second after the pacing pulse. Thus, in various implementations, only the IEGM associated with a test significant event or events needs to be stored in the device 100.

In addition, as discussed further below with reference to FIG. 7, marker data associating the test data and the IEGM is also stored. In the case of the capture threshold test, over the course of several test pulses, pacing amplitude is decreased until loss of capture is identified and then increased until capture is regained. The capture threshold is identified as the amplitude at which capture is regained. For each of the pertinent test pulses, the electrocardiogram and marker data is stored.

A goal of the exemplary method 300 is to reduce the amount of time a care provider spends on a capture threshold assessment. In particular, the intracardiac stimulation device 100 can provide stored test data and IEGMs to the external device 254, which can alleviate the need for generating IEGMs during a follow-up patient consultation. Moreover, by providing marker data, it can further reduce the time necessary to verify test data, as discussed further below. For example, the external device 254 may be a programmer, as is described more fully herein.

While the exemplary method 300 above is discussed with reference to a capture threshold test, other tests, such as amplitude measurement, or other know cardiac tests may be performed. For example, the positive and/or negative amplitude of an evoked response may be measured, and the associated IEGM and marker data stored. Other cardiac tests are possible.

It should be noted that although shown as a single flow, there may be several test events necessary to complete the test. Thus, in some implementations, there may be several cycles of test data measurement and storage, and of IEGM acquisition and storage.

Figure 4:
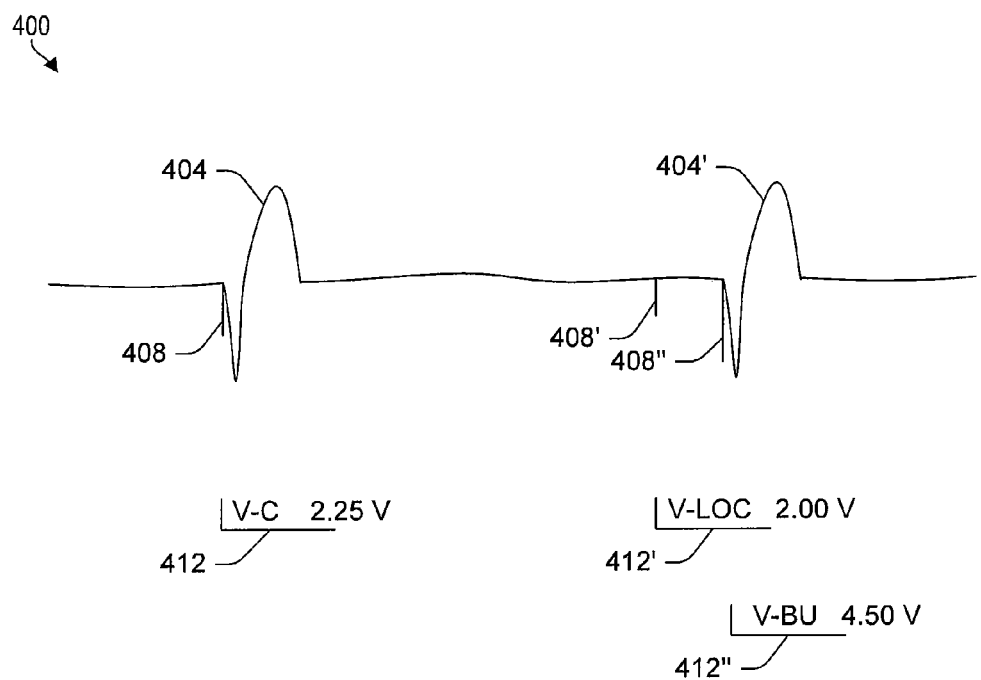
FIG. 4 is a diagram of an exemplary intracardiac electrogram stored in the intracardiac stimulation device.

FIG. 4 shows an exemplary intracardiac event electrogram (IEGM) 400 stored in the intracardiac stimulation device 100 during a threshold test. The IEGM 400 includes a waveform 404 of a cardiac event evoked in response to a pacing pulse 408 that resulted in capture. A second pacing pulse 408', delivered at a later time and with a lesser amplitude, does not evoke a cardiac event and thus corresponds to non-capture. As a result, a third pacing pulse 408" is delivered as a back-up at higher amplitude that aims to ensure capture and a resulting cardiac event represented by the waveform 404'.

The exemplary IEGM further includes markers 412, 412', 412" that indicate ventricular stimulation and capture "V-C", ventricular stimulation and loss of capture "V-LOC", ventricular back-up stimulation with capture "V-BU" and for each marker, pacing pulse amplitude in volts. With respect to the "L" shaped marks, the vertical line indicates time of event and the horizontal line typically indicates refractory period (e.g., refractory period associated with an implanted device). In an auto sensing mode, a refractory marker may indicate that a sensed event was missed. In addition, the pacing pulses 408, 408', 408" may be considered markers because sensing channel "blanking" typically occurs during delivery of a pacing pulse. Such indicia allow for a quick review of the IEGM and one or more corresponding stimulation parameters. Compression of information (e.g., data, markers, etc.) via data reduction or modeling may occur where appropriate.

While various exemplary markers are shown in FIG. 4, other markers may exist. For example, markers may include cardiac markers (e.g., P, R, etc.), pacing markers (e.g., A, V, etc.) and algorithmic markers (e.g., AutoCapture back-up pulses, per-cycle pacing output values, per-cycle measured P/R amplitude values, refractory intervals, etc.). Markers may address several needs. For example, they may let care providers determine if a device's interpretation of cardiac rhythm matches that of a care provider, thereby ensuring that the automatic result is based on a proper foundation; together with one or more IEGMs, markers can support a determination of whether the automatic threshold test was performed using a suitable cardiac rhythm (e.g. not during atrial fibrillation, which can yield misleading atrial sensing and capture test results, or during fusion pacing, in which coincident intrinsic events and pacing can yield similarly invalid results); markers may let care providers ensure that the correct cardiac cycle has been marked as a loss of capture or sensing; and markers can help more closely reproduce the in-clinic threshold test user interface and report printouts, lending greater familiarity to the automatic result for both the programmer operator and (frequently) the separate reviewing care provider. The markers may include special markers indicating that two adjacent event electrograms are not continuous.

Exemplary Programming System

Figure 5:
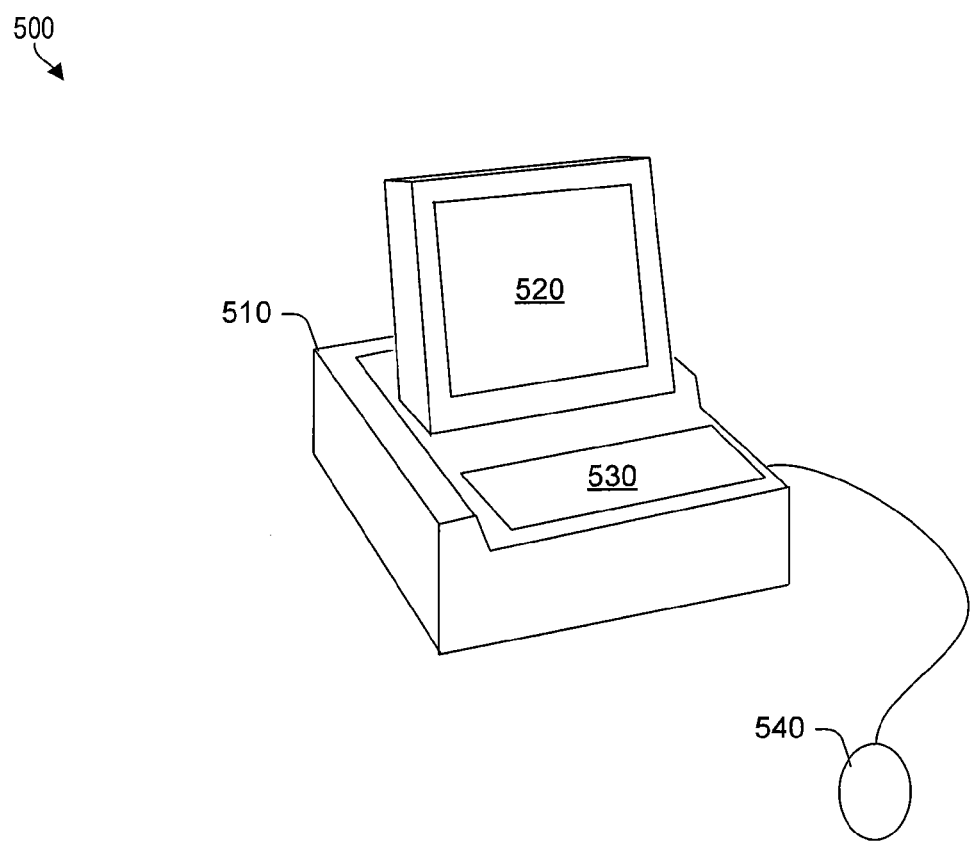
FIG. 5 is a block diagram of an exemplary programming system for communicating with the intracardiac stimulation device.

FIG. 5 shows an exemplary programming system 500 for communicating with the intracardiac stimulation device 100. The programming system 500 may be the external device 254 of FIG. 2 or another device capable of communicating with the intracardiac stimulation device 100 via the telemetry circuit 264. The programming system 500 includes a computing processor 510, a display 520, a keyboard 530 (optional), and a communication device 540. The communication device 540 allows for communication with an implanted device. For example, the communication device 540 may be a telemetry probe. In general, such a telemetry probe is placed in proximity to an implanted device and wireless communication is established. The computing processor 510 may be a special or general purpose computer.

The term "programmer", "programmer device" or "programming system" is commonly used to describe a computing system that includes hardware and software that can operate to communicate with an implanted intracardiac stimulation device. An example of a programming system is the Model 3510 programming system marketed by St. Jude Medical, Inc. (St. Paul, Minn.). Thus, in one example, the exemplary programming system 500 includes various features of the Model 3510 programming system. The Model 3510 programming system includes a custom, portable computer system that features a large, color display on a touch-sensitive, active matrix LCD screen. The Model 3510 programmer can provide continuous, simultaneous display of surface ECGs, intracardiac IEGMs, annotated event markers, and Electronic Calipers™, where an A paced and V sensed interval (e.g., AR interval) is automatically measured and reported, for example, on the programmer screen. The Model 3510 includes a full-size keyboard that allows for easy input of patient and other information. A touch sensitive screen is possible. An automated follow-up feature guides this process and generates custom reports quickly and easily. The programmer then prints reports on a full-size sheet of paper for easy insertion into patient charts. The Model 3510 programming system is lightweight for easy portability. In addition, it can interface with various commercially available data management systems.

More specific features of the Model 3510 programming system include a capability to collect from an implantable device a number of episodes (e.g., 60 episodes, etc.) and a number of minutes of continuous fully annotated stored IEGMs (e.g., 25 minutes, etc.) with a number of seconds of pre-trigger information (e.g., 32 seconds, etc.) as stored by the implantable device; a user-selectable standard automated follow-up protocol and up to 24 customizable automatic follow-up protocols; archive data storage that offers the ability to view and print information acquired during previous follow-up sessions; detection, therapy, and episode summaries; lifetime diagnostics, including pacing and charging history and event, heart rate, and sensor histograms.

As described herein, the exemplary programmer or programming system 500 includes an ability to download IEGM and/or other information from an implantable or implanted device. For example, such an exemplary programming system optionally includes hardware and/or software capable of downloading and displaying the exemplary IEGM 400 of FIG. 4. An exemplary programmer may include a circuit for telemetric transmission of test data, an IEGM, and IEGM information associated with a threshold test wherein the IEGM information includes one or more markers, a display to present at least some of the IEGM information associated with a threshold test and control logic to respond to user input related to a decision to forego a follow-up assessment related to the threshold test. The circuit for telemetric transmission generally operates to receive the test data, IEGM, and IEGM information associated with a threshold test from an intracardiac stimulation device 100. As already mentioned, the IEGM information associated with the threshold test may relate to interactions between a component and tissue.

Figure 6:
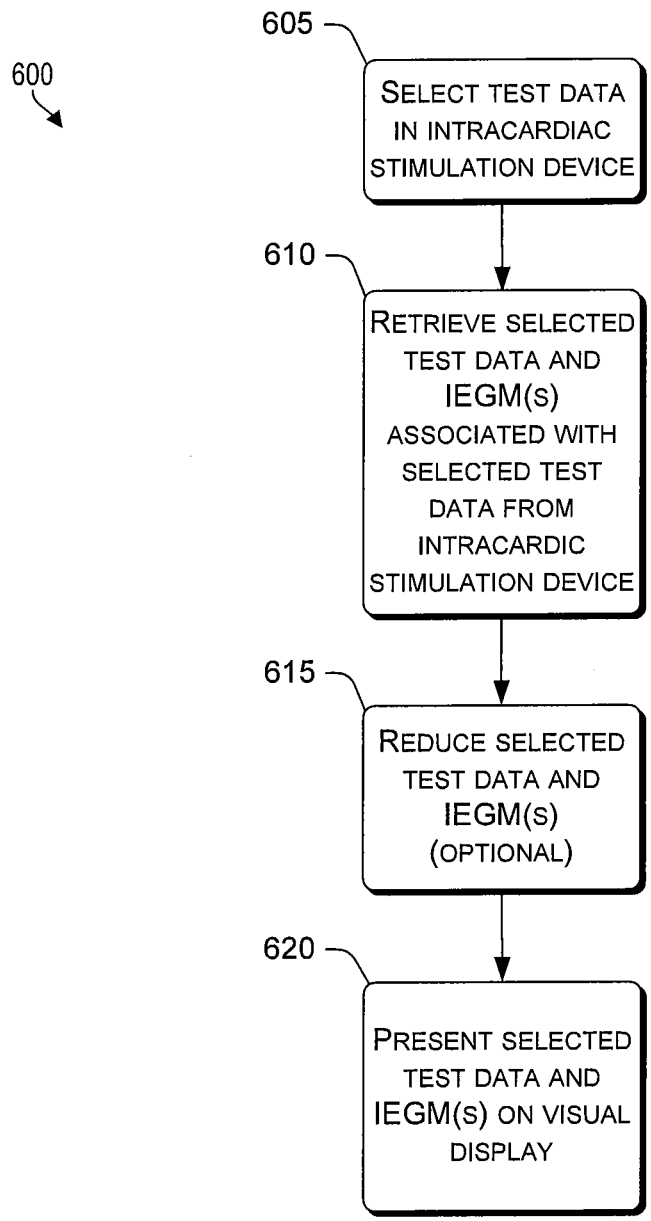
FIG. 6 is a flow chart of an exemplary method for retrieving test data and an intracardiac electrogram from the intracardiac stimulation device.

FIG. 6 shows a flow chart of an exemplary method 600 for retrieving test data and an IEGM from the intracardiac stimulation device 100. In step 605, test data stored in the intracardiac stimulation device 100 is selected. In one embodiment, the programming system 500 selects the test data in the intracardiac stimulation device 100. For example, the programming system 500 may select test data containing a minimum capture threshold or a maximum capture threshold. In step 610, the selected test data is retrieved from the intracardiac stimulation device 100. In one embodiment, the programming system 500 retrieves the test from the intracardiac stimulation device 100 via the telemetry circuit 264 and the communication device 240.

In step 615, the IEGM associated with the test data is retrieved from the intracardiac stimulation device 100. In one embodiment, the programming system 500 retrieves the IEGM associated with the test data from the intracardiac stimulation device 100, and stores the IEGM.

In optional step 620, the IEGM is reduced by selectively removing data from the IEGM. The data removed from the IEGM may include data before the pacing pulse and data after the cardiac event evoked in response to the pacing pulse. In this way, waveforms relevant for verification of the test data remain in the IEGM while extraneous data is removed.

In one embodiment, the programming system 500 analyzes the IEGM and selectively removes data from the IEGM to reduce the IEGM. For example, the programming system 500 may identify a memory address of the cardiac event represented by the IEGM, select a memory address window around the cardiac event in the IEGM, and retrieve a portion of the IEGM within the memory address window. Reduction of the IEGM may include use of statistics, models, histograms, templates, and other such methods and techniques. In another embodiment, the programming system 500 reduces the IEGM before retrieving the IEGM from the intracardiac stimulation device in step 610.

In step 620, the test data and the IEGM are presented on a visual display. A patient care provider can then verify the test data based on the IEGM during a follow-up patient consultation without generating an IEGM during the consultation. In one embodiment, the programming system 500 presents the test data and the IEGM on the display 520.

The exemplary method 600 may retrieve and present multiple IEGMs together with the associated test data on the visual display. For example, the exemplary method 600 may retrieve IEGMs and test data periodically stored in the intracardiac stimulation device 100, and simultaneously display some or all of the IEGMs and associated test data.

Figure 7:
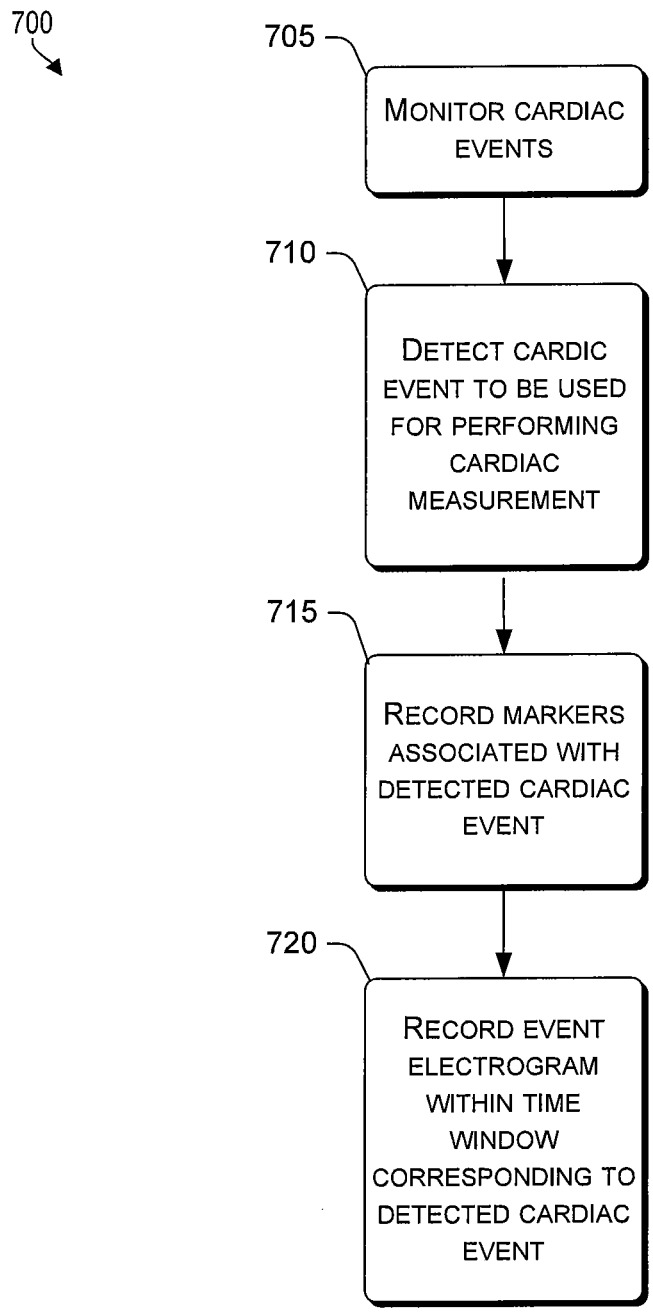
FIG. 7 is a flow chart of an exemplary method for storing test data in the intracardiac stimulation device.

FIG. 7 shows a flow chart of an exemplary method 700 for storing test data in the intracardiac stimulation device 100. In step 705, cardiac events are monitored. In one embodiment, the device 100 monitors the cardiac events. In step 710, cardiac events to be used for performing a cardiac measurement are detected. In one embodiment, the device 100 detects the cardiac events to be used for performing the cardiac measurement. In step 715, markers associated with the detected cardiac event are recorded. In one embodiment, the memory 260 records the markers by storing the markers. In step 720, an IEGM within a time interval corresponding to the detected cardiac event is recorded. In one embodiment, the IEGM is recorded by storing the IEGM in the memory 260. Although shown in separate blocks 715 and 720, the markers and IEGMs may be stored concurrently.

Referring to FIG. 7, during an out-of-clinic test, such as during atrial autocapture for example, the intracardiac stimulation device 100 determines when to start storing data by monitoring cardiac events 705. When the intracardiac stimulation device 100 detects an event (in this example—an atrial pacing pulse) that will be used to perform a measurement 710, it records the event electrogram 720 and records the markers associated with the detected cardiac event 715. In some implementations, the event electrogram is recorded within a window corresponding to the detected cardiac event 720, such as, for example, up to about one second of data before and about one second after the detected cardiac event. The intracardiac stimulation device 100 then continues monitoring events but does not record data in memory until it detects the next event that will be used to perform another measurement pertinent to the test. In this manner, only relevant, non contiguous data is stored in the memory 260.

During a subsequent follow-up visit, the programmer retrieves the complexes and displays at least a portion of the complex as stored by the intracardiac stimulation device 100, which may depend on the event type (P-wave versus QRS complex for example).

Figure 8:
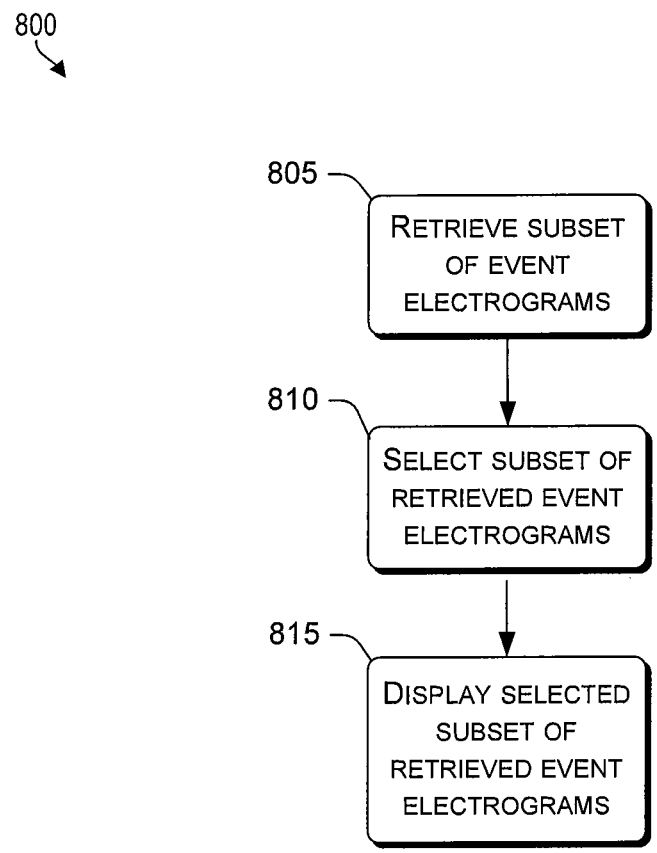
FIG. 8 is a flow chart of an exemplary method for displaying event electrograms.

FIG. 8 shows a flow chart of an exemplary method 800 of reducing IEGMs. In step 805, a subset of IEGMs is retrieved from the intracardiac stimulation device 100. In one embodiment, the programming system 500 (FIG. 5) retrieves the subset of IEGMs from the intracardiac stimulation device 500 via the communication device 540 (FIG. 5). In step 810, a subset of the retrieved IEGMs is selected. In one embodiment, the computing processor 510 of the programming system 500 selects the subset of retrieved IEGMs. In step 815, at least a portion of the selected subset of retrieved IEGMs is displayed. In one embodiment, the programming system 500 displays the selected subset of retrieved IEGMs on the display 520 (FIG. 5).

FIG. 9 shows a flow diagram of a method 900 of data storage and retrieval of IEGM data 920 for display. IEGM data 920 occurring during a cardiac test measurement are selectively stored, in the intracardiac stimulation device 100, as event IEGMs 915. The event IEGMs occur within a time interval corresponding to a detected cardiac event/events associated with the test measurement. A subset of the event IEGMs 915, or the entire set of the stored event IEGMs 915, are retrieved from the intracardiac stimulation device 100. This may be accomplished using a communication device 540 (shown in FIG. 5), for example. The retrieved IEGMs 910, or a smaller subset of the retrieved IEGMs 910, may be displayed at 905 for test data verification, or other purposes. In some embodiments, the test measurement data also may be present along with the IEGMs 920, 915, 910, and 905. In this way, the IEGM data 920 for an entire test may be reduced to a much smaller subset for storage, download, and/or display purposes.

Thus, in some embodiments, the intracardiac stimulation device 100, determines which complexes are relevant and only stores those complexes. As such, some embodiments reduce follow-up times by saving retrieval time, and allow data to be presented in clear and concise manner. Further, a more efficient usage of device memory is possible in some embodiments.

In some embodiments, the device 100 may store IEGM data at lower rate than it is sampled by the device 100. This is to conserve memory. For example, the device 100 may only store every 4 samples. Throwing away three quarters of the data, however, can reduce the fidelity of the displayed waveform. This can cause P and R wave amplitudes, for example, to appeared to be fluctuating due to under-sampling (storing). To reduce the perceived fluctuations, in some implementations, the data that would have been omitted is evaluated, and only the peak data is selected for storage and display, rather than merely selecting a sample at a specific time. Thus, IEGM data is stored if it corresponds to a peak during a sample interval. This can greatly improve the fidelity of the displayed waveform, and does not increase the storage size.

The embodiments described herein are illustrative of the present invention. As these embodiments of the present invention are described with reference to illustrations, various modifications or adaptations of the methods and/or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is to be understood that the present invention is not limited to only the embodiments illustrated.

What is claimed is:

1. An intracardiac stimulation device comprising:
a) a memory; and
b) a processor such that the intracardiac stimulation device is capable of:
performing an out-of-clinic test;
automatically recording in the intracardiac stimulation device a measured test result from the out-of-clinic test into the memory;
recording in the intracardiac stimulation device non-contiguous electrogram data corresponding with cardiac event complexes used to determine the measured test result into the memory;
recording in the intracardiac stimulation device marker data associated with the non-contiguous electrogram data into the memory;
transmitting the non-contiguous electrogram data and marker data to an external device; and
displaying on a visual display at least a portion of the non-contiguous electrogram data and marker data in clinic.

2. The intracardiac stimulation device of claim 1, wherein the processor is such that the intracardiac stimulation device is capable of storing marker data indicating when adjacent electrogram data are not contiguous.

3. The intracardiac stimulation device of claim 1, wherein the processor is such that the intracardiac stimulation device is capable of recording event electrogram data if the event electrogram data corresponds to a peak during a sampling interval.

4. The intracardiac stimulation device of claim 1, wherein the measured test result comprises at least one of: (a) a capture threshold; or (b) an amplitude.

* * * * *